US009526910B2

(12) United States Patent
 Crutchfield et al.

(10) Patent No.: US 9,526,910 B2
(45) Date of Patent: *Dec. 27, 2016

(54) THERAPY DELIVERY METHOD AND SYSTEM FOR IMPLANTABLE MEDICAL DEVICES

(71) Applicant: Medtronic, Inc., Minneapolis, MN (US)

(72) Inventors: Randolph E Crutchfield, Scottsdale, AZ (US); Lonny V Cabelka, San Clemente, CA (US); Mark R Boone, Gilbert, AZ (US); Marshall J Rasmussen, Mesa, AZ (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/536,881

(22) Filed: Nov. 10, 2014

(65) Prior Publication Data
US 2015/0134021 A1    May 14, 2015

Related U.S. Application Data

(62) Division of application No. 13/626,988, filed on Sep. 26, 2012, now Pat. No. 8,886,314.

(51) Int. Cl.
*A61N 1/39* (2006.01)
*A61N 1/37* (2006.01)

(52) U.S. Cl.
CPC .............. *A61N 1/3981* (2013.01); *A61N 1/371* (2013.01); *A61N 1/3906* (2013.01); *A61N 1/3956* (2013.01); *A61N 1/3987* (2013.01)

(58) Field of Classification Search
CPC .... A61N 1/371; A61N 1/3906; A61N 1/3956; A61N 1/3981; A61N 1/3987

(Continued)

(56) References Cited

U.S. PATENT DOCUMENTS 3,258,013 A * 6/1966 Druz .................... A61N 1/39
                                                                607/2
3,527,229 A * 9/1970 Kempen ............... A61N 1/39
                                                                607/5

(Continued)

FOREIGN PATENT DOCUMENTS

EP        0569616 B1    6/1992
EP        0985427 A1    3/2000

OTHER PUBLICATIONS (PCT/US2013/061516) PCT Notification of Transmittal of the International Search Report and the Written Opinion of the International Searching Authority, Mailed Jan. 7, 2014, 11 pages.

(Continued)

*Primary Examiner* — Christopher A Flory
(74) *Attorney, Agent, or Firm* — Evans M. Mburu

(57) ABSTRACT

Recent advancements in power electronics technology have provided opportunities for enhancements to circuits of implantable medical devices. The enhancements have contributed to increasing circuit miniaturization and an increased efficiency in the operation of the implantable medical devices. The therapy delivery circuits and techniques of the disclosure facilitate generation of a therapy stimulation waveform that may be shaped based on the patient's physiological response to the stimulation waveform. The generated therapy stimulation waveforms include a stepped leading-edge that may be shaped having a varying slope and varying amplitudes associated with each of the segments of the slope. Unlike the truncated exponential waveform delivered by the conventional therapy delivery circuit which is based on the behavior of the output capacitors (i.e., i=C(dV/dt)), the stimulation waveform of the present disclosure may be dynamically shaped as a function of an individual patient's response. The dynamically shaped therapy stimulation waveforms facilitate achieving lower (Continued)

capture thresholds which reduces the device's supply consumption thereby increasing longevity of the device and facilitate a reduction of tissue damage.

15 Claims, 11 Drawing Sheets

(58) Field of Classification Search
USPC .................. 607/2, 5, 7, 9, 17, 28, 29, 37
See application file for complete search history.

(56) References Cited

U.S. PATENT DOCUMENTS

| | | | |
|---|---|---|---|
| 3,775,658 A * | 11/1973 | Miles | A61N 1/39 200/286 |
| 4,180,078 A | 12/1979 | Anderson | |
| 4,548,209 A | 10/1985 | Wielders et al. | |
| 5,163,427 A | 11/1992 | Keimel | |
| 5,188,105 A | 2/1993 | Keimel | |
| 5,193,535 A | 3/1993 | Bardy et al. | |
| 5,265,588 A | 11/1993 | Nelson et al. | |
| 5,354,316 A | 10/1994 | Keimel | |
| 5,385,575 A | 1/1995 | Adams | |
| 5,449,377 A | 9/1995 | Adams et al. | |
| 5,464,434 A | 11/1995 | Alt | |
| 5,470,345 A | 11/1995 | Hassler et al. | |
| 5,507,781 A | 4/1996 | Kroll et al. | |
| 5,545,186 A | 8/1996 | Olson et al. | |
| 5,609,618 A * | 3/1997 | Archer | A61N 1/385 607/74 |
| 5,643,324 A | 7/1997 | Persson | |
| 5,683,432 A | 11/1997 | Goedeke et al. | |
| 5,709,711 A * | 1/1998 | Fain | A61N 1/3943 607/8 |
| 5,713,924 A | 2/1998 | Min et al. | |
| 5,830,236 A | 11/1998 | Mouchawar et al. | |
| 5,836,976 A | 11/1998 | Min et al. | |
| 5,855,593 A | 1/1999 | Olson et al. | |
| 5,891,172 A | 4/1999 | Stendahl et al. | |
| 5,906,633 A * | 5/1999 | Mouchawar | A61N 1/3956 128/908 |
| 5,913,877 A | 6/1999 | Kroll et al. | |
| 5,978,706 A * | 11/1999 | Brewer | A61N 1/39 607/5 |
| 6,094,597 A | 7/2000 | Wold | |
| 6,125,300 A | 9/2000 | Weijand et al. | |
| 6,230,056 B1 | 5/2001 | Kroll | |
| 6,233,483 B1 | 5/2001 | Causey, III et al. | |
| 6,236,882 B1 | 5/2001 | Lee et al. | |
| 6,438,422 B1 | 8/2002 | Schu et al. | |
| 6,512,940 B1 | 1/2003 | Brabec et al. | |
| 6,522,915 B1 | 2/2003 | Ceballos et al. | |
| 6,546,287 B1 * | 4/2003 | Havel | A61N 1/3937 607/7 |
| 6,622,046 B2 | 9/2003 | Fraley et al. | |
| 6,714,818 B1 * | 3/2004 | Fishler | A61N 1/3956 607/5 |
| 6,745,073 B1 * | 6/2004 | Kroll | A61N 1/3956 607/5 |
| 6,763,266 B1 * | 7/2004 | Kroll | A61N 1/3956 607/5 |
| 6,954,669 B1 | 10/2005 | Fishier et al. | |
| 7,174,208 B2 | 2/2007 | DeGroot et al. | |
| 7,647,095 B2 | 1/2010 | Bhunia | |
| 7,805,189 B2 | 9/2010 | Stein et al. | |
| 8,391,964 B2 | 3/2013 | Musley et al. | |
| 8,532,785 B1 * | 9/2013 | Crutchfield | A61N 1/3981 607/59 |
| 8,886,314 B2 * | 11/2014 | Crutchfield | A61N 1/3987 607/17 |
| 9,168,379 B2 * | 10/2015 | Cabelka | A61N 1/362 |
| 2003/0125773 A1 | 7/2003 | Havel et al. | |
| 2006/0122657 A1 | 6/2006 | Deal et al. | |
| 2010/0030288 A1 | 2/2010 | Bonner et al. | |
| 2010/0030290 A1 | 2/2010 | Bonner et al. | |
| 2010/0114248 A1 | 5/2010 | Donofrio et al. | |
| 2010/0114258 A1 | 5/2010 | Donofrio et al. | |
| 2010/0217366 A1 * | 8/2010 | Moulder | A61N 1/37 607/119 |
| 2012/0041500 A1 | 2/2012 | Zhu et al. | |
| 2014/0088656 A1 | 3/2014 | Cabelka et al. | |

OTHER PUBLICATIONS

Chinese Office Action mailed Apr. 11, 2016, 5 pages, English translation.

Chinese Office Action mailed Apr. 11, 2016, 6 pages, Chinese translation.

* cited by examiner

THERAPY DELIVERY METHOD AND SYSTEM FOR IMPLANTABLE MEDICAL DEVICES

FIELD

The disclosure relates to body implantable medical devices and, more particularly to circuits and techniques for generating therapy stimulation waveforms.

BACKGROUND

A wide variety of implantable medical devices (IMDs) that employ electronic circuitry for providing various therapies such as electrical stimulation of body tissue, monitoring a physiologic condition, and/or providing a substance are known in the art. For example, cardiac pacemakers and implantable cardioverter-defibrillators (ICDs) have been developed for maintaining a desired heart rate during episodes of bradycardia or for applying cardioversion or defibrillation therapies to the heart upon detection of serious arrhythmias. Other devices deliver drugs to the brain, muscle and organ tissues, and/or nerves for treatment of a variety of conditions.

Over the past 20 years, the IMDs have evolved from relatively bulky, crude, and short-lived devices to complex, long-lived, and miniaturized IMDs that are steadily being miniaturized with their functionality continuously increasing. For example, numerous improvements have been made in cardioversion/defibrillation leads and electrodes that have enabled the cardioversion/defibrillation energy to be precisely delivered about selected upper and lower heart chambers and thereby dramatically reducing the delivered shock energy required to cardiovert or defibrillate the heart chamber. Moreover, the high voltage output circuitry has been improved in many respects to provide monophasic, biphasic, or multi-phase cardioversion/defibrillation stimulation (shock or pulse) waveforms that are efficacious, sometimes with particular combinations of cardioversion/defibrillation electrodes, in lowering the required shock energy to cardiovert or defibrillate the heart.

The miniaturization of IMDs is driving size and cost reduction of all IMD components including the electronic circuitry components, where it is desirable to reduce the size so that the overall circuitry can be more compact. The IMDs are powered by an internal power source, typically one or more batteries, that serves a variety of functions, including, but not limited to, supplying power to electronic components and circuitry and charging high voltage capacitors that are discharged through medical electrical leads into the heart to regulate heart rhythms. The functional sophistication and complexity of the IMD operating systems powered by the battery have increased over the years.

Despite the advances, battery powered IMDs must be replaced when the battery becomes depleted, and therefore conserving battery power remains important to maintain or prolong the life of the IMD. Therefore, as the dimensions of the IMDs decreases, the electronic circuits of the IMD circuitry are preferred to decrease power consumption in order to maintain or increase longevity.

SUMMARY

The efforts toward increased miniaturization of implantable medical devices have been impeded by the goal of advancing the technological capability of the devices. Often, improvements to the technical performance of the device are achieved by complex circuitry that requires an increase in the component count—this results in an increase in the overall foot print of device circuitry and power consumption, among other things.

Stimulation therapy waveforms generated in accordance with aspects of the present disclosure are dynamically configured to have a stepped/ramped leading edge. The waveforms have been shown to reduce the capture thresholds for therapy, thereby expending less power than that required for capture using conventional therapy stimulation waveforms.

In an embodiment, an improved therapy delivery circuit generates a stimulation therapy waveform that includes an approximated stepped/ramp leading edge. The therapy delivery circuit includes a plurality of capacitors that are stacked in one of multiple dynamically-alterable configurations and coupled to a delivery bridge for delivery of the therapy.

In one embodiment, a controller is provided for dynamically controlling the stacking of the capacitors. In a first configuration, the capacitors are stacked in a parallel configuration. In a second configuration, the capacitors are individually coupled to the delivery bridge, in sequential order to form a series configuration, for discharge to provide the therapy. An interval is provided between the coupling of each individual capacitor to the delivery bridge. That is to say that each of the capacitors is successively connected to another capacitor—that is already coupled to the delivery bridge—to form a serially stacked configuration of the plurality of capacitors. The controller is programmed to determine duration for the successive stacking of each individual capacitor.

In accordance with one exemplary embodiment, a switching circuit is provided for coupling the plurality of capacitors in one of multiple stacking configurations. In the embodiment, the switching circuit includes a field effect transistor (FET) coupled to one terminal of a given capacitor for coupling the given capacitor to a common node of the circuit to form the parallel configuration with the others of the plurality of capacitors. The switching circuit further includes a switch for coupling the given capacitor in series with another of the plurality of capacitors. In some embodiments, the switch may be a triac.

In another embodiment, a method for generating a therapy stimulation waveform having a ramped leading edge is disclosed. In the method, the plurality of capacitors are discharged through the electrodes of an implantable medical lead. In one embodiment, the capacitors are sequentially coupled to the electrodes in a series configuration to discharge the stored energy for delivery of therapy. An interval is provided between the coupling of each individual capacitor to form the series configuration of the plurality of capacitors. The magnitude of the intervals between the coupling of individual capacitors defines a slope of the stepped leading edge of the stimulation waveform.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals/letters denote like elements, and.

DETAILED DESCRIPTION

The following detailed description is illustrative in nature and is not intended to limit the embodiments of the invention or the application and uses of such embodiments. Furthermore, there is no intention to be bound by any expressed or implied theory presented in the preceding technical field, background, brief summary or the following detailed description.

In the present disclosure, the inventors have disclosed circuits and techniques associated with generating therapy stimulation energy having varying waveforms for the delivery of therapies such as pacing, defibrillation and cardioversion by an implantable medical device. The configurable waveforms of the therapy stimulation generated in accordance with aspects of this disclosure include a ramped or stepped leading edge that mimics the cell response behavior for a given patient. The waveforms reduce the thresholds required to achieve capture, thereby increasing the efficiency and effectiveness of the implantable medical therapies.

Figure 1:
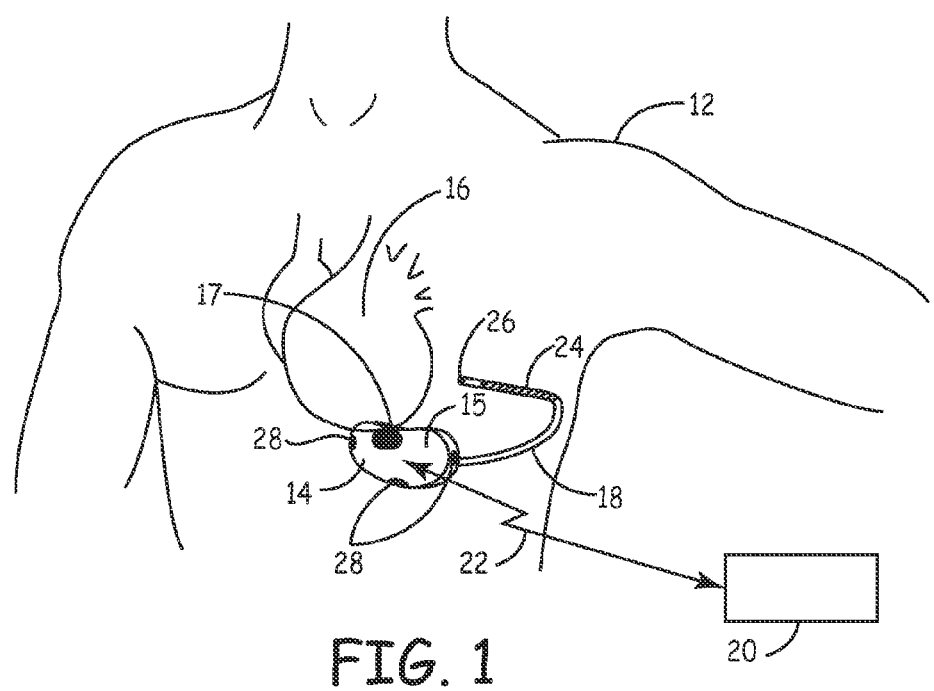
FIG. 1 is a schematic diagram of a medical device.

FIG. 1 is a schematic diagram of an exemplary medical device in which the present invention may be usefully practiced. As illustrated in FIG. 1, the present invention may be utilized in an implantable medical device 14 that includes a housing 15 containing circuitry for operating device 14 that is subcutaneously implanted in a patient, outside the ribcage of patient 12, anterior to the cardiac notch, for example. According to an embodiment, housing 15 may be implanted in the pectoral region of the patient 12. Further, device 14 may include a subcutaneous sensing and cardioversion/defibrillation therapy delivery lead 18 coupled to the device 14 that is tunneled subcutaneously into a location adjacent to a portion of a latissimus dorsi muscle of patient 12. Specifically, lead 18 is tunneled subcutaneously from the median implant pocket of device 14 laterally and posterially to the patient's back to a location opposite the heart such that the heart 16 is disposed between the device 14 and the distal electrode coil 24 and distal sensing electrode 26 of lead 18.

It is understood that while the subcutaneous device 14 is shown positioned through loose connective tissue between the skin and muscle layer of the patient, the term "subcutaneous device" is intended to include a device that can be positioned in the patient to be implanted using any non-intravenous location of the patient, such as below the muscle layer or within the thoracic cavity, for example.

Further referring to FIG. 1, programmer 20 is shown in telemetric communication with device 14 by wireless communication link 22. Communication link 22 may be any appropriate wireless link such as Bluetooth, NFC, WiFi, MICS, or as described in U.S. Pat. No. 5,683,432 "Adaptive Performance-Optimizing Communication System for Communicating with an Implantable Medical Device" to Goedeke, et al.

Device 14 may be constructed from stainless steel, titanium or ceramic as described in U.S. Pat. No. 4,180,078 "Lead Connector for a Body Implantable Stimulator" to Anderson and U.S. Pat. No. 5,470,345 "Implantable Medical Device with Multi-layered Ceramic Enclosure" to Hassler, et al. The electronics circuitry of device 14 may be incorporated on a polyamide flex circuit, printed circuit board (PCB), ceramic substrate with integrated circuits packaged in leadless chip carriers, chip scale packaging, and/or wafer scale packaging.

Lead 18, which is inserted within a connector (not shown) positioned on housing 15 to electrically couple the lead to the circuitry located in housing 15, includes a distal defibrillation coil electrode 24, a distal sensing electrode 26, an insulated flexible lead body and a proximal connector pin (not shown) for connection to housing 15 via the connector. In some embodiments, distal sensing electrode 26 may be sized appropriately to match the sensing impedance of one or more electrodes 28 that are positioned along housing 15 to form a housing-based subcutaneous electrode array with electrodes 28 positioned to form orthogonal signal vectors.

Device 14 in an embodiment of the present invention includes miniaturized circuitry for providing therapy, as described in detail below. Optical hemodynamic sensor 17 is preferably a multiple waveform oximeter, such as a pulse oximeter or a mixed-venous oxygen sensor, for example. Electrodes 28 and optical sensor 17 are welded into place on the outer surface of the housing 15 and are connected via wires (not shown) to electronic circuitry (described herein below) located inside housing 15. Electrodes 28 may be constructed of flat plates, or alternatively, spiral electrodes as described in U.S. Pat. No. 6,512,940 "Subcutaneous Spiral Electrode for Sensing Electrical Signals of the Heart" to Brabec, et al., and mounted in a non-conductive surround shroud as described in U.S. Pat. No. 6,522,915 "Surround Shroud Connector and Electrode Housings for a Subcutaneous Electrode Array and Leadless ECGs" to Ceballos, et al and U.S. Pat. No. 6,622,046 "Subcutaneous Sensing Feedthrough/Electrode Assembly" to Fraley, et al.

The electronic circuitry employed in device 14 can take any of the known forms that detect a tachyarrhythmia from the sensed ECG and provide cardioversion/defibrillation shocks as well as post-shock pacing as needed while the heart recovers. An exemplary simplified block diagram of such circuitry adapted to function employing the first and second cardioversion-defibrillation electrodes as well as the ECG sensing and pacing electrodes described herein below is set forth in U.S. Pat. No. 7,647,095, "Method and Apparatus for Verifying a Determined Cardiac Event in a Medical Device Based on Detected Variation in Hemodynamic Status" to Bhunia incorporated herein by reference in its entirety. It will be understood that the simplified block diagram does not show all of the conventional components and circuitry of such devices including digital clocks and clock lines, low voltage power supply and supply lines for powering the circuits and providing pacing pulses or telemetry circuits for telemetry transmissions between the device 14 and external programmer 20.

Figure 2:
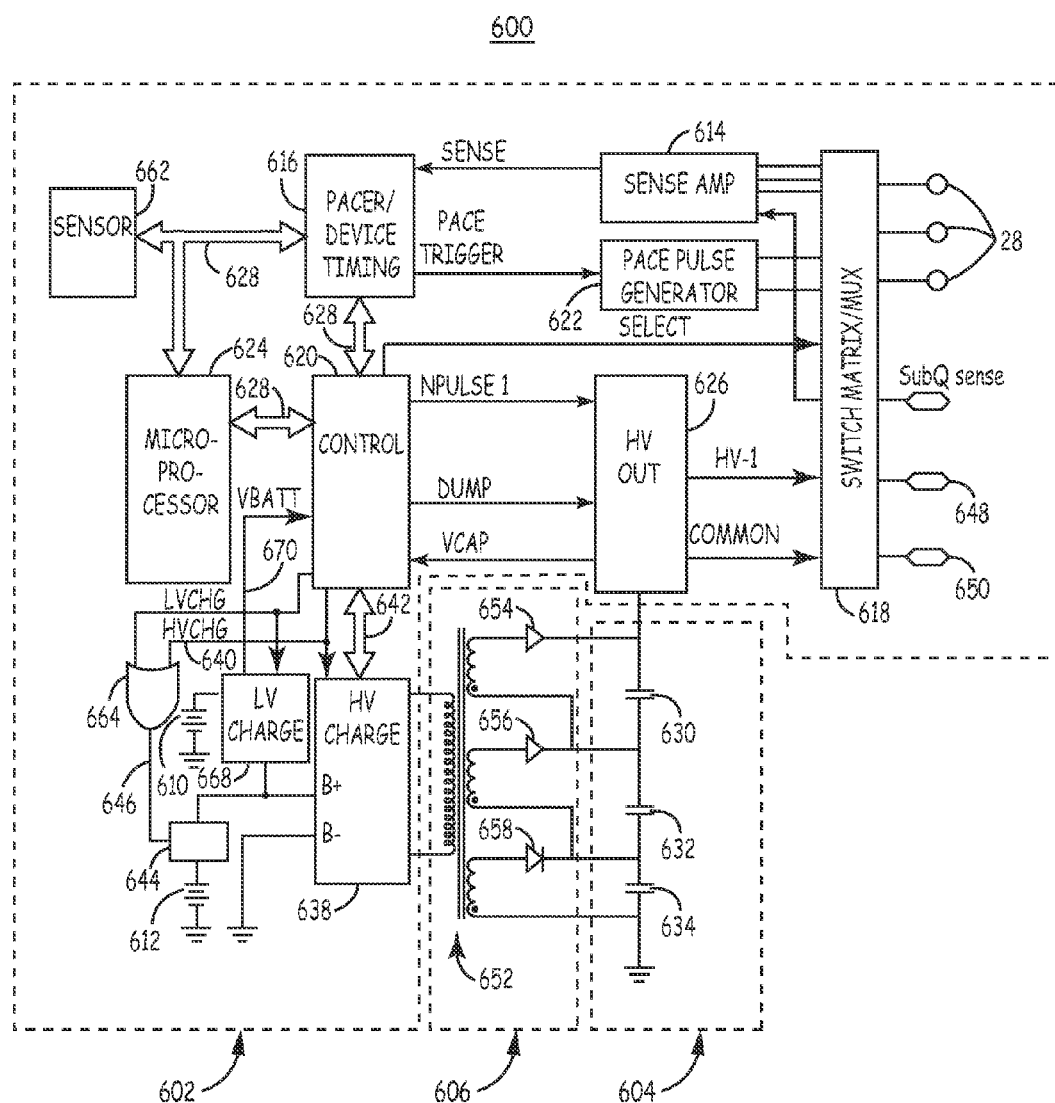
FIG. 2 is a schematic diagram of prior art electronic circuitry included in exemplary medical devices including a conventional charge circuit.

FIG. 2 is a schematic diagram of a prior art electronic circuitry 600 included in exemplary medical devices having a conventional capacitor configuration and employing a conventional transformer coupling for charging the capacitors. The electronic circuitry includes software, firmware and hardware that cooperatively monitor the ECG, determine when a cardioversion-defibrillation shock or pacing is necessary, and deliver prescribed cardioversion-defibrillation and pacing therapies. Many of the aspects of the prior art electronic circuitry and in particular those shown in the region defined by the enclosed dashed line 602 may suitably be used in conjunction with the aspects set forth in the exemplary embodiments of the present disclosure.

As illustrated in FIG. 2, the electronic circuitry 600 includes one or more power sources such, for example, as a low voltage battery 610 and a high voltage battery 612. Low voltage battery 610 powers the device circuitry and the pacing output capacitors to supply pacing energy in a manner well known in the art. The low voltage components, such as those associated with pacing, are charged to a pre-programmed voltage level by a low-voltage charging circuit 668 under control of the signal VBATT provided on line 670. Low voltage supply 668 provides regulated power to the low voltage ICs, hybrid circuits, and discrete components of the electronic circuit.

It is understood that although the prior art system of FIG. 2 includes both low and high power therapy, the present invention may be employed in a device that provides only one therapy, such as a high power defibrillation therapy, for example.

In FIG. 2, sense amp 614 in conjunction with pacer/device timing circuit 616 processes the far field ECG sense signal that is developed across a particular ECG sense vector defined by a selected pair of the subcutaneous electrodes 28 or, optionally, a virtual signal if selected. The selection of the sensing electrode pair is made through the switch matrix/MUX 618 in a manner to provide the most reliable sensing of the EGM signal of interest, which would be the R wave for patients who are believed to be at risk of ventricular fibrillation. The far field ECG signals are passed through the switch matrix/MUX 618 to the input of the sense amplifier 614 that, in conjunction with pacer/device timing circuit 616, evaluates the sensed EGM. Bradycardia, or asystole, is typically determined by an escape interval timer within the pacer timing circuit 616 and/or the control circuit 620. Pace trigger signals are applied to the pacing pulse generator 622 generating pacing stimulation when the interval between successive R-waves exceeds the escape interval. Bradycardia pacing is often temporarily provided to maintain cardiac output after delivery of a cardioversion-defibrillation shock that may cause the heart to slowly beat as it recovers back to normal function. Sensing subcutaneous far field signals in the presence of noise may be aided by the use of appropriate denial and extensible accommodation periods as described in U.S. Pat. No. 6,236,882 "Noise Rejection for Monitoring ECGs" to Lee, et al.

Detection of a malignant tachyarrhythmia is determined in the control circuit 620, for example, as a function of the intervals between R-wave sense event signals that are output from the pacer/device timing 616 and sense amplifier circuit 614 to the timing and control circuit 620. Supplemental sensors such as tissue color, tissue oxygenation, respiration, patient activity and the like may be used to contribute to the decision to apply or withhold a defibrillation therapy as described generally in U.S. Pat. No. 5,464,434 "Medical Interventional Device Responsive to Sudden Hemodynamic Change" to Alt. Sensor processing unit 662 provides sensor data to microcomputer 624 via data bus 628.

Certain steps in the performance of the detection algorithm criteria are cooperatively performed in microcomputer 624, including microprocessor, RAM and ROM, associated circuitry, and stored detection criteria that may be programmed into RAM via a telemetry interface (not shown). Data and commands are exchanged between microcomputer 624 and timing and control circuit 620, pacer timing/amplifier circuit 616, and high voltage output circuit 626 via a bi-directional data/control bus 628. The pacer timing/amplifier circuit 616 and the control circuit 620 are clocked at a slow clock rate. The microcomputer 624 is normally asleep, but is awakened and operated by a fast clock by interrupts developed by each R-wave sense event, on receipt of a downlink telemetry programming instruction or upon delivery of cardiac pacing pulses to perform any necessary mathematical calculations, to perform tachycardia and fibrillation detection procedures, and to update the time intervals monitored and controlled by the timers in pacer/device timing circuitry 616.

The algorithms and functions of the microcomputer 624 and control circuit 620 employed and performed in detection of tachyarrhythmias are set forth, for example, in commonly assigned U.S. Pat. No. 5,354,316 "Method and Apparatus for Detection and Treatment of Tachycardia and Fibrillation" to Keimel; U.S. Pat. No. 5,545,186 "Prioritized Rule Based Method and Apparatus for Diagnosis and Treatment of Arrhythmias" to Olson, et al, U.S. Pat. No. 5,855,593 "Prioritized Rule Based Method and Apparatus for Diagnosis and Treatment of Arrhythmias" to Olson, et al and U.S. Pat. No. 5,193,535 "Method and Apparatus for Discrimination of Ventricular Tachycardia from Ventricular Fibrillation and Treatment Thereof" to Bardy, et al. Particular algorithms for detection of ventricular fibrillation and malignant ventricular tachycardias can be selected from among the comprehensive algorithms for distinguishing atrial and ventricular tachyarrhythmias from one another and from high rate sinus rhythms that are set forth in the '316, '186, '593 and '535 patents.

The detection algorithms are highly sensitive and specific for the presence or absence of life threatening ventricular arrhythmias, e.g., ventricular tachycardia (VT) and ventricular fibrillation (VF). When a malignant tachycardia is detected, high voltage capacitors 630, 632 and 634 are charged to a pre-programmed voltage level by a high-voltage charging circuit 638. It is generally considered inefficient to maintain a constant charge on the high voltage output capacitors 630, 632 and 634. Instead, charging is initiated when control circuit 620 issues a high voltage charge command HVCHG delivered on line 640 to high voltage charge circuit 638 and charging is controlled by means of bi-directional control/data bus 642 and a feedback signal VCAP from the HV output circuit 626. High voltage output capacitors 630, 632 and 634 may be of film, aluminum electrolytic or wet tantalum construction.

The negative terminal of high voltage battery 612 is directly coupled to common ground (Vcc). Switch circuit 644 is normally open so that the positive terminal of high voltage battery 612 is disconnected from the positive power input of the high voltage charge circuit 638. The high voltage charge command HVCHG is also conducted via conductor 646 to the control input of switch circuit 644, and switch circuit 644 closes in response to connect positive high voltage battery voltage EXT B+ to the positive power input of high voltage charge circuit 638. Switch circuit 644 may be, for example, a field effect transistor (FET) with its source-to-drain path interrupting the EXT B+ conductor 646 and its gate receiving the HVCHG signal on conductor 640. High voltage charge circuit 638 is thereby rendered ready to begin charging the high voltage output capacitors 630, 632, and 634 with charging current from high voltage battery 612. In embodiments having both pacing and cardioversion/defibrillation, the circuit may be implemented with OR gate 664 to switch between a LVCHG signal and the HVCHG signal.

High voltage output capacitors 630, 632, and 634 may be charged to very high voltages, e.g., 700-3150V, to be discharged through the body and heart between the electrode pair of subcutaneous cardioversion-defibrillation electrodes 648 and 650. High voltage capacitors 630, 632 and 634 are charged by high voltage charge circuit 638 and a high frequency, high-voltage transformer 652 as described in detail in commonly assigned U.S. Pat. No. 4,548,209 "Energy Converter for Implantable Cardioverter" to Wielders, et al. Proper charging polarities are maintained by diodes 654, 656 and 658 interconnecting the multiple secondary windings of high-voltage transformer 652 respectively associated with the capacitors 630, 632, and 634. As noted above, the state of capacitor charge is monitored by circuitry within the high voltage output circuit 626 that provides a VCAP, feedback signal indicative of the voltage to the timing and control circuit 620. Timing and control circuit 620 terminates the high voltage charge command HVCHG when the VCAP signal matches the programmed capacitor output voltage, i.e., the cardioversion-defibrillation peak shock voltage.

Control circuit 620 then develops control signal NPULSE 1 that is applied to the high voltage output circuit 626 for triggering the delivery of cardioverting or defibrillating shocks. In particular, the NPULSE 1 signal triggers discharge of the capacitor 630, 632 and 634. In this way, control circuitry 620 serves to control operation of the high voltage output stage 626, which delivers high energy cardioversion-defibrillation shocks between the pair of the cardioversion-defibrillation electrodes 648 and 650 coupled to the HV-1 and COMMON output.

Thus, device 14 monitors the patient's cardiac status and initiates the delivery of a cardioversion-defibrillation shock through the cardioversion-defibrillation electrodes 648 and 650 in response to detection of a tachyarrhythmia requiring cardioversion-defibrillation. The high HVCHG signal causes the high voltage battery 612 to be connected through the switch circuit 644 with the high voltage charge circuit 638 and the charging of output capacitors 630, 632, and 634 to commence. Charging continues until the programmed charge voltage is reflected by the VCAP signal, at which point control and timing circuit 620 sets the HVCHG signal low terminating charging and opening switch circuit 644. Typically, the charging cycle takes only fifteen to twenty seconds, and occurs very infrequently. The device 14 can be programmed to attempt to deliver cardioversion shocks to the heart in the manners described above in timed synchrony with a detected R-wave or can be programmed or fabricated to deliver defibrillation shocks to the heart in the manners described above without attempting to synchronize the delivery to a detected R-wave. Episode data related to the detection of the tachyarrhythmia and delivery of the cardioversion-defibrillation shock may be stored in RAM for uplink telemetry transmission to an external programmer as is well known in the art to facilitate in diagnosis of the patient's cardiac state. A patient receiving the device 14 on a prophylactic basis would be instructed to report each such episode to the attending physician for further evaluation of the patient's condition and assessment for the need for implantation of a more sophisticated implantable cardio-defibrillator device (ICD). In other embodiments, no storage of episode data will take place.

Figure 3:
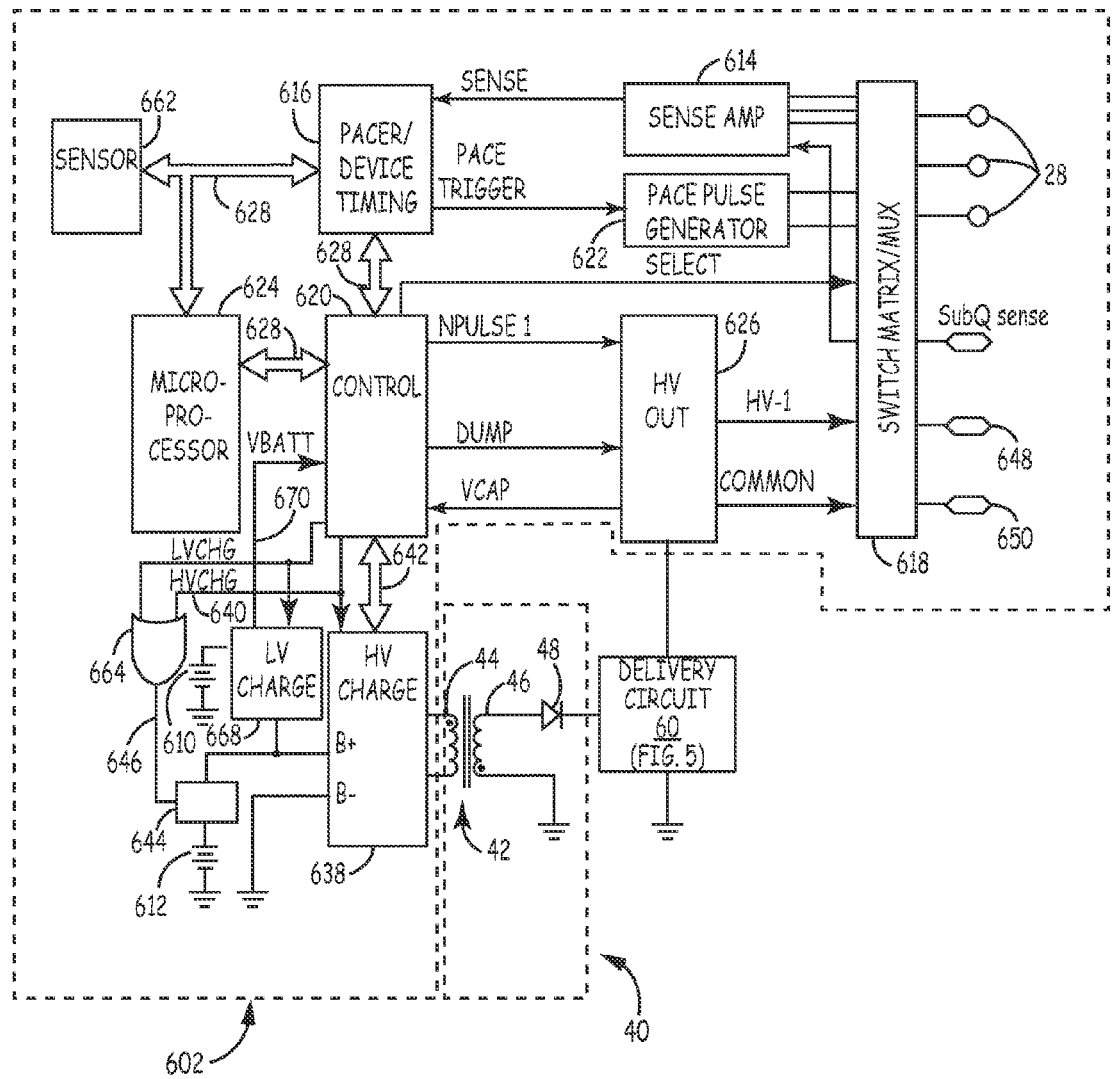
FIG. 3 is a schematic illustrating one embodiment of a charge circuit in accordance with the present disclosure.

FIG. 3 is a schematic illustrating one embodiment of a charge circuit 40 in accordance with the present disclosure. The charge circuit 40 can be coupled to the elements in the region 602 shown in FIG. 2 or similar IMD systems in accordance with the present invention. As illustrated in FIG. 2, the conventional charge circuit 606 includes a transformer 652 with a primary winding 652a and multiple secondary windings 652b, 652c and 652d. The number of the secondary windings corresponds to the number of output capacitors for holding charge for delivery of therapy by the IMD. In other words, conventional IMD circuits having the output capacitors hardwired in series have required multiple secondary transformer windings to charge up the capacitors to the desired voltage level.

The inventors have observed that the requirement to provide multiple secondary transformer windings has translated to transformers that are bulky. Moreover, the supply voltage required to charge the output capacitors in the conventional charge circuit must be kept at a relatively high value because of the serial arrangement of the output capacitors requiring multiple transformer secondary windings to be coupled to each of the output capacitors. In the conventional charge circuit, the supply voltage provided is typically on the order of 700 V to 1000 V. One of the benefits of the reduction in the charge voltage is that it facilitates a reduction in size as well as the stress placed on the charging components.

Returning to FIG. 3, charge circuit 40 is illustrated having a transformer 42 including a single primary winding 44 and a single secondary winding 46. The single secondary winding 46 is coupled to a delivery circuit through a single diode 48. In accordance with further aspects of the present disclosure, the delivery circuit includes a plurality of output capacitors that are controlled by a coupling circuit 64 (FIG. 5) and 164 (FIG. 6) that controls the coupling of the plurality of capacitors. As used in this disclosure, a plurality refers to an integer number of two or more.

Figure 5:
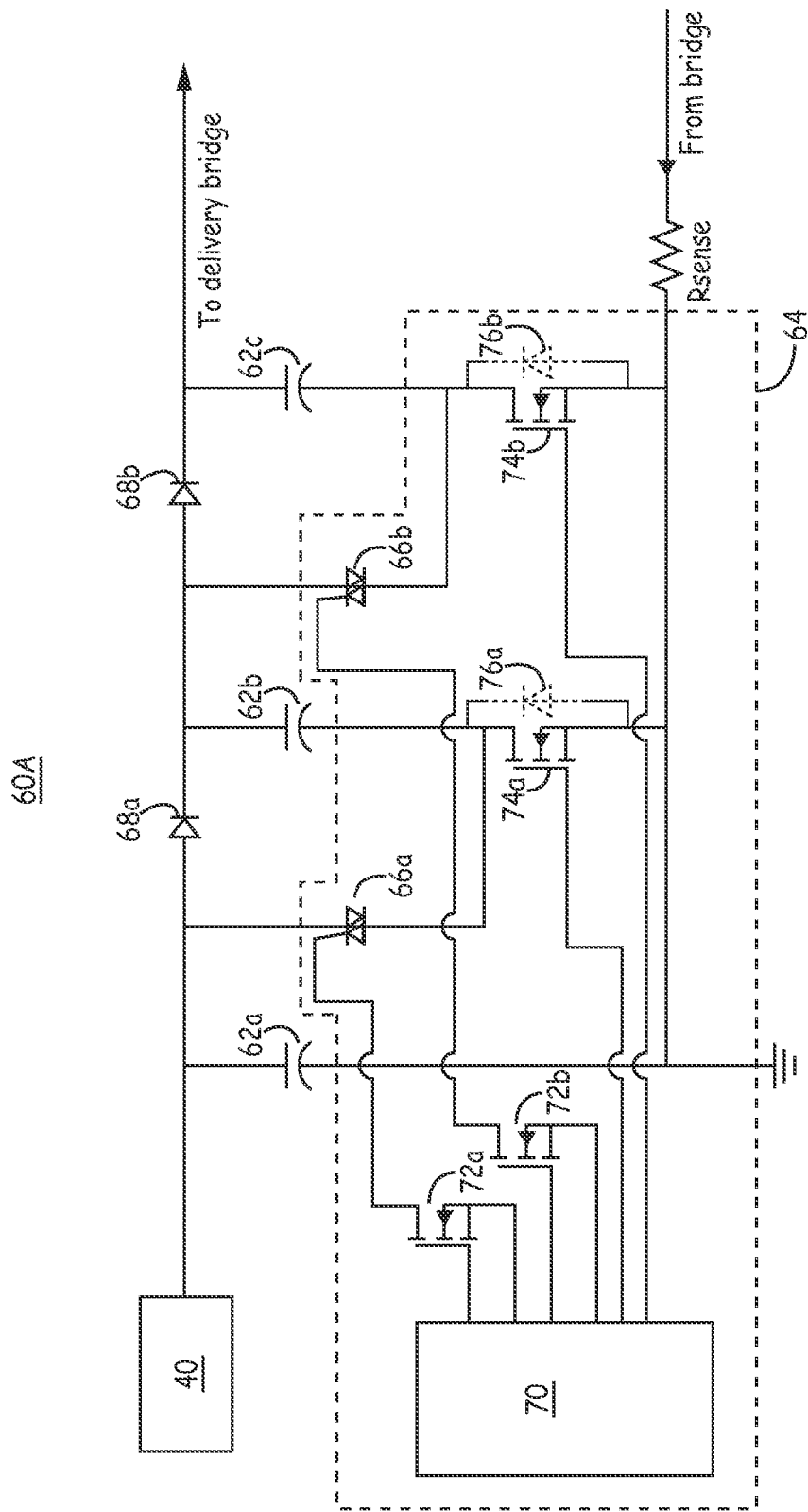
FIG. 5 depicts a therapy delivery circuit of a charge circuit in accordance with an embodiment of the present disclosure.
Figure 6:
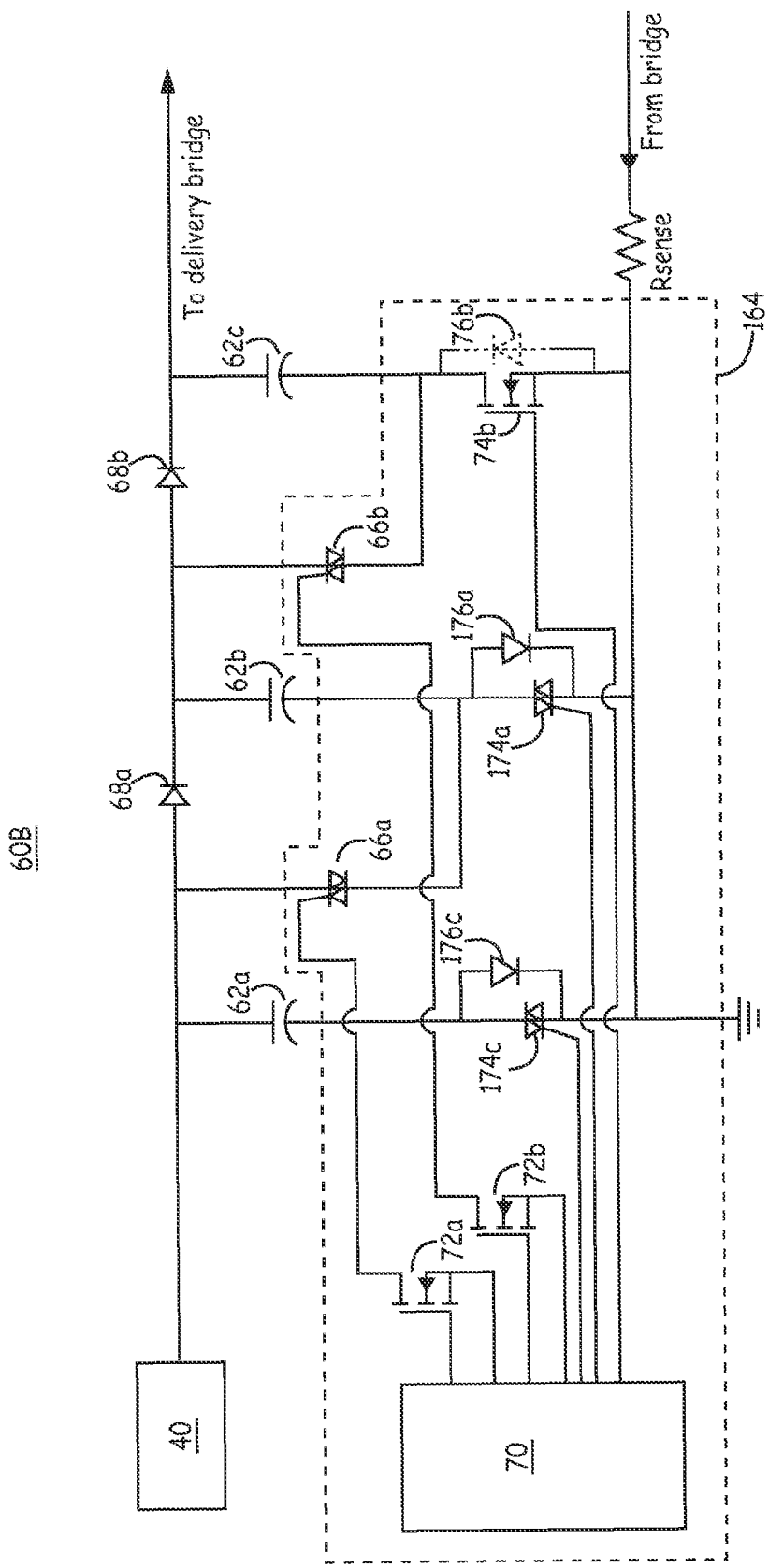
FIG. 6 depicts a therapy delivery circuit of a charge circuit in accordance with an alternate embodiment of the present disclosure.

The details of the stacking operation of the coupling circuits are described in further detail in FIGS. 5 and 6. Briefly, the coupling circuit stacks the output capacitors in a stacking configuration selected from one of multiple stacking configurations including a series configuration, parallel configuration, or a combination series and parallel configuration during various time periods. For example, the output capacitors may be stacked in a parallel configuration during the charge-up of the output capacitors to the supply voltage level. Prior to or subsequent to the charging of output capacitors, the coupling circuit may couple the output capacitors in any other desired stacking configurations. The charging of the output capacitors may be performed in any known manner, including a "flyback" fashion. One such manner is set forth in commonly assigned U.S. Pat. No. 5,265,588, incorporated herein by reference in its entirety.

The stacking of the output capacitors in a parallel configuration during charging reduces the supply voltage required to charge the capacitors. In the presently described embodiment, the supply voltage required to charge the output capacitors, can be reduced to about 250 V in comparison to the conventional charge circuit 602. The reduction in the voltage requirement also facilitates a reduction in the voltage rating of components associated with the charge circuit 40 as well as a reduction in the component count which may improve reliability of the implantable medical device.

The details of the construction of the transformer are not critical to the understanding of embodiments of the present disclosure and can be in accordance with any known methodologies. However, utilizing a transformer 42 having a single primary winding and single secondary winding as described in accordance with embodiments of the present invention, facilitates a reduction in the size of the transformer required to charge up the output capacitors. The space otherwise occupied by the additional secondary windings of transformers such as that of the charge circuit 602 and the corresponding additional diodes coupled to the output capacitors can be allocated to other components for added functionality or can facilitate a reduction in the overall footprint of the charge circuit 40.

Figure 4:
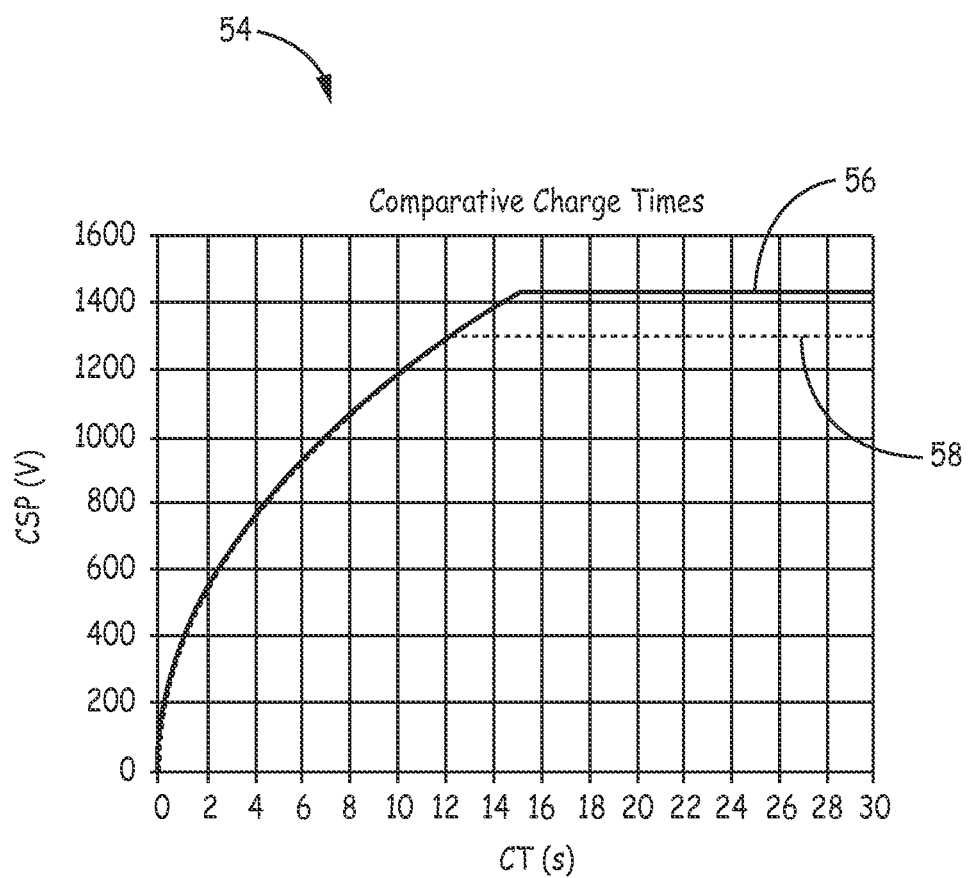
FIG. 4 is an exemplary graph showing results of comparative analysis of charging durations for a conventional charge circuit and a charge circuit in accordance with the present disclosure.

FIG. 4 is an exemplary graph showing results of comparative analysis of charging durations for a conventional charge circuit and a charge circuit in accordance with the present disclosure. Graph 54 depicts a first trace 56 and a second trace 58 that are plotted on an X, Y axis chart. The horizontal (X) axis of graph 54 represents the time in seconds and the vertical (Y) axis represents the energy in volts.

The first trace 56, illustrated as a solid line, represents a plot of the conventional charge circuit 602 charging up the output capacitors that are coupled in series to the supply voltage. The second trace 58, illustrated as dotted line, represents a plot of the charge circuit 40 charging up the output capacitors coupled in parallel to the supply voltage.

The traces 56, 58 comparatively illustrate the relative charge durations for the conventional charge circuit and a charge circuit in accordance with the present disclosure. In this example, the charge circuit is charging to a reduced energy level as a result of the reduced threshold requirements, which is facilitated by the delivery of a modified stimulation waveform in accordance with the present disclosure. As shown in graph 54, the charge circuit 40 takes a comparatively shorter time to charge up the output capacitors to the supply voltage relative to the time taken by the conventional charge circuit 602.

FIGS. 5 and 6 depict therapy delivery circuits 60a, 60b (collectively "60") in accordance with alternate embodiments of the present disclosure. The exemplary therapy delivery circuits 60 generate therapy stimulation having dynamically configurable waveforms that may be customized based on the patient's physiological response. Such therapy stimulation waveforms may be generated having a stepped leading-edge.

As previously discussed in FIG. 3, the delivery circuit 60 is coupled to the charge circuit 40 via diode 48. Delivery circuit 60 includes a plurality of output capacitors 62a, 62b, and 62c, (collectively "output capacitors 62"). The output capacitors 62 are charged by the charge circuit 40 and hold the energy for generating therapy stimulation waveforms.

In accordance with the present disclosure, the stacking of the output capacitors 62 relative to one another is dynamically configurable. At least one of the output capacitors 62 is coupled to the coupling circuit. The coupling circuit dynamically configures the output capacitors to form various parallel and series combinations.

Figure 5A:
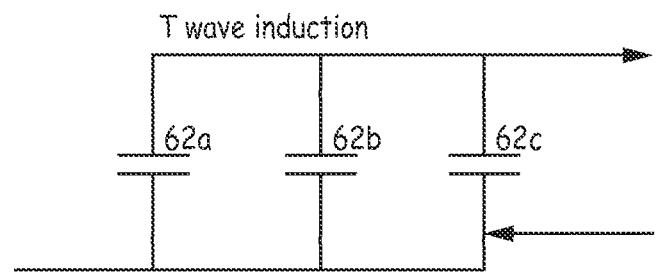
FIG. 5A depicts a functional equivalent circuit of the stacking of the output capacitors of FIG. 5 in a first configuration.
Figure 5B:
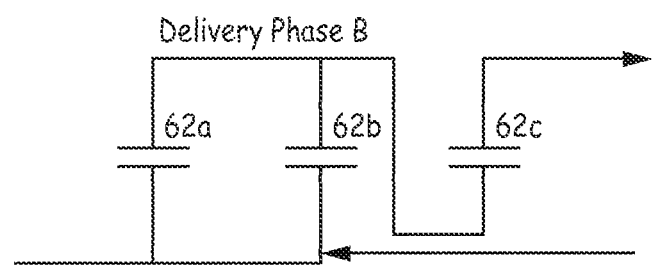
FIG. 5B depicts a functional equivalent circuit of the stacking of the output capacitors of FIG. 5 in a second configuration.
Figure 5C:
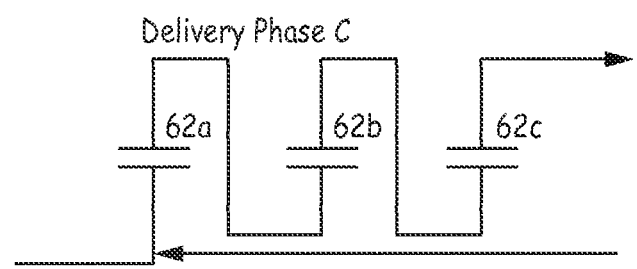
FIG. 5C depicts a functional equivalent circuit of the stacking of the output capacitors of FIG. 5 in a third configuration.

FIG. 5 describes an embodiment in which delivery of therapy is initiated with the plurality of output capacitors 62 being coupled in parallel. This embodiment may be utilized to induce ventricular fibrillation in a patient during implantation to facilitate defibrillation threshold testing. The output capacitors may subsequently be reconfigured in accordance with the dynamic reconfiguration techniques of the present disclosure for therapy delivery. For ease of reference, the description of FIG. 5 is discussed in conjunction with the circuit diagrams illustrated in FIGS. 5A-5C. Each of FIGS. 5A-5C depicts the functional equivalent circuit subsequent to the coupling of the output capacitors for different phases of therapy delivery in accordance with the embodiment of FIG. 5.

Turning to the embodiment of FIG. 5, a first switch, such as triac 66a, has a first terminal that is coupled to the negative terminal of capacitor 62b and a second terminal of triac 66a is coupled to the positive terminal of capacitor 62a, the cathode of diode 48 and an anode of diode 68a. The coupling circuit 64 also includes a second triac 66b that is coupled at a first terminal to the negative terminal of capacitor 62c and at a second terminal between the positive terminal of the capacitor 62b, the cathode of diode 68a and an anode of diode 68b. The diodes 68a, 68b maintain the discharge polarity by setting the direction for flow of charge of the therapy stimulation energy.

The coupling circuit 64 further includes a delivery control module 70. The gates of triacs 66a, 66b are coupled to the delivery control module 70 through gate triggered field effect transistors (FETs) 72a, 72b respectively. The delivery control module 70 activates or deactivates the FETs 72 (switch to an "ON" or "OFF" position, respectively) to control the stacking configuration of the output capacitors 62. The selective activation or deactivation of the FETs 72 will switch the triacs 66 ON or OFF (activate or deactivate), respectively. The delivery control module 70 may further be coupled to FETs 74a, 74b that connect the output capacitors 62b and 62c, respectively, to the common ground (Vcc). Diodes 76a and 76b, illustrated in phantom lines, represent the effective intrinsic body diodes of FETs 74a and 74b respectively.

In one embodiment, the output capacitors 62 may be stacked in a first configuration such that all the capacitors are coupled in parallel. Stacking of the output capacitors 62 in the parallel configuration is achieved by turning FETs 74 ON and by turning triacs 66 OFF. The output capacitors 62 may then be charged in this parallel configuration to a predetermined voltage level. As described in FIG. 3, the charging polarity (i.e., the direction for the flow of current from the charge circuit 40 to the output capacitors 62) is set by diode 48. The output capacitor 62a is charged via the diode 48 with a connection to common ground. Output capacitor 62b is charged through the diode 48, diode 68a, through FET 74a with a connection to common ground. Output capacitor 62c is charged through the diode 48, diode 68a, diode 68b, through FET 74b with a connection to common ground. In some embodiments, a minimal voltage drop relative to the overall charge voltage may be observed for output capacitors 62b, 62c due to the charging through diodes 68. However, such voltage difference is analogous to the voltage difference arising from the mismatch in the individual secondary transformer windings for each capacitor in the conventional circuit.

Subsequent to a confirmation that the output capacitors 62 are fully charged, the coupling circuit 64 configures the output capacitors 62 in a desired stacking configuration to initiate the delivery of therapy. For example, the output capacitors 62 may remain in the first configuration or the configuration may be changed from the first configuration to a second configuration that is different from the first. Even further, the present disclosure facilitates the dynamic reconfiguration of the output capacitors 62 from the second to a third and, even further, to other subsequent configurations during therapy delivery. As such, the output capacitors 62 are configured in a given one of multiple configurations prior to or, during therapy delivery. The discharge of energy by the output capacitors 62 in any given configuration coincides with a distinct therapy delivery phase.

The therapy is delivered through electrodes that may be coupled to the delivery circuit 60 through a delivery bridge, provided in HV out 62b, for example. The operation of the delivery bridge does not impact the operation of the present invention and is therefore not shown or discussed. In essence, the delivery bridge comprises switches that configure a delivery path that includes the electrodes. In other words, the delivery bridge directs flow of therapy stimulation energy to the heart and back to the IMD in a unipolar or bipolar electrode configuration as is described in detail in published literature. The therapy stimulation energy may be discharged from the output capacitors through the electrodes in multiple phases such that capacitor 62a discharges through diodes 68a, 68b; capacitor 62b discharges through diode 68b; and capacitor 62c discharges directly via the delivery bridge.

In one embodiment, therapy delivery is initiated with the output capacitors 62 remaining in the first configuration. In other words, the output capacitors 62a, 62b, and 62c are stacked in a parallel configuration for a predetermined interval of time. In this first phase, the output capacitors 62a, 62b, and 62c are decoupled from the charge circuit and coupled to the electrodes (not shown) to initiate discharge of the capacitors for delivery of a first phase of the therapy. FIG. 5A depicts a functional equivalent circuit of the stacking of output capacitors 62 in the first configuration. As is shown in FIG. 5A, the output capacitors 62 are coupled in parallel and the common terminals of the capacitors connect to the delivery bridge. The equivalent circuit of FIG. 5A is achieved by configuring the FETs 74 in an ON position and by turning OFF the triacs 66.

As stated above, the coupling of the output capacitors 62 may be reconfigured from the first configuration to a second configuration following discharge of the output capacitors during the duration of the first predetermined interval. It is contemplated that the duration of time from initiation of discharge to the reconfiguration of the output capacitor coupling may be selectively varied to provide a desired waveform. Further, the waveform may be shaped by varying the configuration of the stacking of capacitors for each interval, keeping in mind that the output capacitors may be reconfigured individually or in any combination to achieve a stacking configuration for the second, third, and subsequent therapy delivery phases.

Continuing with the illustrative embodiment, the stacking of one of the capacitors, such as output capacitor 62c may be reconfigured for the second configuration. The reconfiguration couples the output capacitor 62c in series with the parallel combination of capacitors 62a and 62b after an interval (first predetermined interval) following the initiation of the discharge of part of the energy in the capacitors 62a, 62b, and 62c in the first phase. The equivalent circuit for the second configuration is depicted in FIG. 5B. The series coupling of capacitor 62c to the parallel coupled capacitors 62a and 62b is performed by turning triac 66b to the ON position while turning FET 74b OFF. The reconfiguration of the stacking of the output capacitors 62a, 62b and 62c to couple capacitor 62c in series initiates the second phase of the therapy delivery. The first predetermined interval is defined to correspond with a point in time during the discharge of the output capacitors 62 that will provide a desired ramp profile for the stimulation waveform. Turning OFF the FET 74b prevents shorting through ground in response to turning triac 66b ON to couple output capacitor 62c in series with the parallel combination of output capacitors 62a, 62b.

In the illustrative embodiment, some of the energy in output capacitors 62 is discharged during a second predetermined interval for a second phase of the therapy delivery. The capacitors may again be reconfigured into a third configuration that provides for stacking all three of the output capacitors in series. In particular, output capacitor 62b is placed in series with output capacitor 62a. The equivalent circuit for the third configuration is depicted in FIG. 5C. The series coupling of capacitor 62a to capacitor 62b is performed by turning triac 66a to the ON position while turning FET 74a OFF. Triac 66b remains in the ON position and FET 74b remains in the OFF position.

FIG. 6 depicts an alternative embodiment of a delivery circuit. The delivery of therapy in accordance with the embodiment of FIG. 6 is initiated with discharge of a first, single, capacitor. The other output capacitors of the plurality of capacitors may subsequently be coupled in series with the first capacitor in accordance with the dynamic reconfiguration techniques of the present disclosure for therapy delivery.

For ease of reference, the description of FIG. 6 is discussed in conjunction with the circuit diagrams illustrated in FIGS. 6A-6E. Each of the circuits in FIGS. 6A-6E depict the functional equivalent of the coupling of the output capacitors for different phases of therapy delivery in accordance with the embodiment of FIG. 6. Furthermore, the elements of delivery circuit 60B of FIG. 6 corresponding to those of delivery circuit 60a in FIG. 5 are numbered with identical reference designators. The reader is referred to the preceding description of FIG. 5 for a full discussion pertaining to those components.

The delivery circuit 60b of FIG. 6 includes a triac 174a that is coupled between output capacitor 62b and ground. A diode 176a is coupled in parallel with triac 174a with the diode 176a cathode is connected to ground. A triac 174c is further coupled between output capacitor 62a and ground. A diode 176c is coupled in parallel with triac 174c and the diode 176c cathode is connected to ground. Both triacs 174a and 174c are connected to the delivery control module 70.

Although it is not depicted as such in the illustrative embodiment, alternative embodiments may include reconfiguration of the terminals of the triacs 174a, 174c with or without additional protection circuitry for connecting the triacs to the delivery control module 70. Such protection circuitry may include FETs with the coupling being similar to that of the coupling of triacs 66.

Figure 6A:
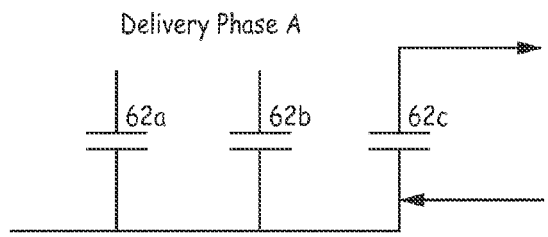
FIG. 6A depicts a functional equivalent circuit following the stacking of the output capacitors of FIG. 6 in accordance with a first configuration.

In the embodiment of FIG. 6, a first phase of therapy delivery is initiated with only a single one of the output capacitors delivering the energy for the stimulation therapy. In this embodiment, the output capacitors 62 are not stacked during the first phase; that is, all triacs 66a, 66b, 174a and 174c are set in the OFF position. Output capacitor 62c is coupled to the electrodes (not shown) for discharge of energy during the first phase. The equivalent circuit of output capacitors 62 is depicted in FIG. 6A. The duration over which the energy is discharged may be predetermined such that only part of the charge stored in the output capacitor 62c is discharged during a first interval.

Figure 6B:
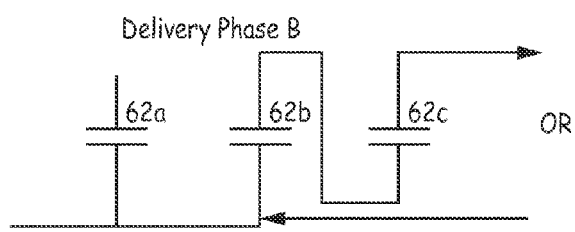
FIGS. 6B and 6C depict alternative functional equivalent circuits following the stacking of the output capacitors of FIG. 6 in accordance with a second configuration.
Figure 6C:
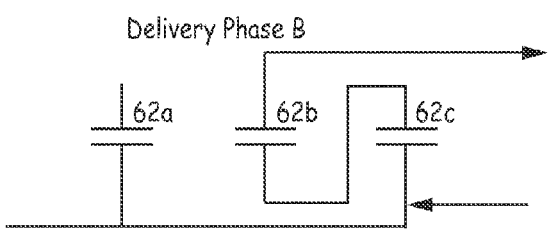

At the expiration of the first interval, a second of the output capacitors, e.g., 62b may be stacked in series with the first capacitor 62c for a second phase of the therapy delivery. The representative equivalent alternative circuits following the coupling of output capacitor 62b in series to capacitor 62c are depicted in FIGS. 6B and 6C. In the second phase, capacitor 62c may be stacked on top of capacitor 62b by turning FET 74b OFF and triacs 66b and 174a ON.

The duration of the first predetermined interval may be set to correspond with a point in time during the discharge of the output capacitor 62c to provide a desired ramp profile for the stepped leading edge of the stimulation waveform.

A second predetermined interval may be provided to define the duration during which some of the energy in the serially coupled capacitors 62b and 62c is discharged. The duration of the second predetermined interval may be measured beginning when the second capacitor, capacitor 62b in this example, is coupled to the first capacitor.

Following the expiration of the second predetermined interval, a third capacitor, capacitor 62a in this example, is connected in series to the serially coupled capacitors 62b and 62c. The coupling of capacitor 62a initiates a third phase of the therapy delivery.

Figure 7:
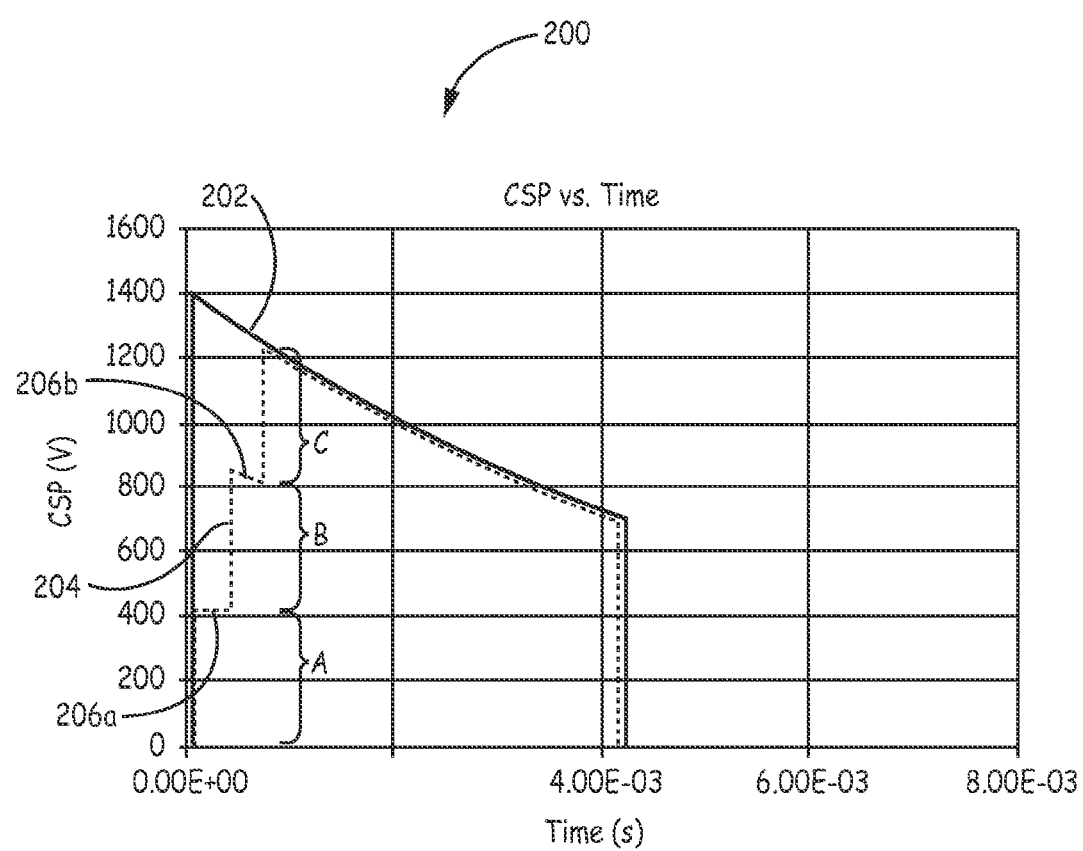
FIG. 7 depicts an exemplary graph illustrating the amplitude of therapy stimulation energy during discharge of the energy stored in a plurality of output capacitors.

A simulation of the therapy stimulation waveform generated during discharge of the output capacitors 62 in the exemplary first, second and third phases of FIG. 6 is described in conjunction with FIG. 7.

Figure 6D:
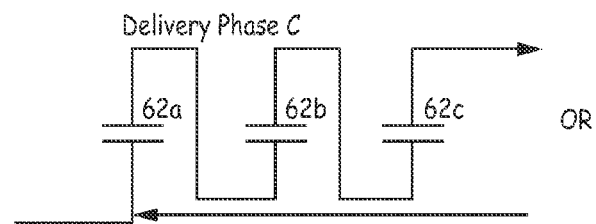
FIGS. 6D and 6E depict alternative functional equivalent circuits following the stacking of the output capacitors of FIG. 6 in accordance with a third configuration.
Figure 6E:
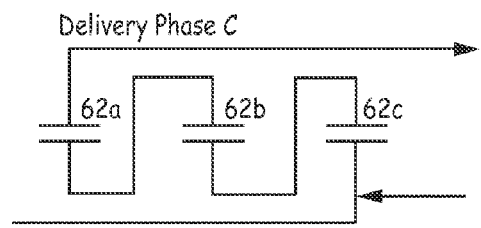

In the illustrative embodiment of FIG. 6, the series coupling of capacitor 62a to the serially connected capacitors 62c and 62b may performed by turning triac 174a OFF, while turning triac 66a ON and triac 174c ON. Triac 66b remains in the ON position. This implementation stacks the combination of output capacitors 62c and 62b on top of output capacitor 62a. FIGS. 6D and 6E depict the alternative equivalent circuits for the output capacitors following the series coupling of capacitor 62a to the serially connected capacitors 62b and 62c.

In other implementations, the delivery of therapy may be initiated in the first phase with discharge of a different first output capacitor (other than 62c). While not illustrated, such alternative implementations may also include additional components and/or the delivery control module 70 may be programmed to provide different control signals.

In the exemplary embodiment, the delivery control module 70 is programmed with the durations for the first and second intervals that control the point in time during the delivery of the therapy stimulation energy when the output capacitors' stacking is reconfigured. The selective control over the first and second intervals enables the discharge profile of the resulting stimulation waveform generated from the energy stored in the output capacitors 62 to be manipulated to emulate the heart cell response time for a given patient and thereby provide efficient threshold levels to ensure capture. Therefore, the dynamic configurability of the stacking of output capacitors 62 coupled with the control of the coupling intervals facilitates generation of stimulation waveforms of varying profiles that can be modified to optimize the therapy based on the heart cell response for different patient populations.

The exemplary coupling circuits of FIGS. 5 and 6 include various switching components that are dynamically controlled to couple the output capacitors in the various stacking configurations. In the illustrative embodiment, the switching components facilitate in the coupling of the three output capacitors to which they are connected to form the various stacking configurations discussed above. The switching components may be grouped such that the components associated with the stacking of each capacitor relative to the other capacitors are defined as a stacking circuit module set. For example, a first set in FIG. 5 may include triac 66a, gate trigger FET 72a, discharge FET 74a while a second set may include triac 66b, gate trigger FET 72b, and discharge FET 74b. As can be deduced from the illustrations of FIGS. 5 and 6, the number of stacking circuit module sets is one less than the number of capacitors in the delivery circuit.

In alternative embodiments, a different number of output capacitors 62 may be provided to define different stimulation waveforms with different delivered energy, slopes or ramp profiles. In such embodiments, additional sets of stacking circuit modules may be provided, as described above, may be included in the coupling circuits 64, 164 to dynamically control the stacking of the additional capacitors during the charging and discharging operations of such additional output capacitors.

The therapy delivery in accordance with the present disclosure facilitates generation of a therapy stimulation waveform that may be shaped based on the patient's physiological response to the stimulation waveform. Unlike the conventional waveform delivered by the conventional therapy delivery circuit which is based on the behavior of the output capacitors (i.e., i=C(dV/dt)), the stimulation waveform of the present disclosure may be dynamically shaped as a function of an individual patient's response. In so doing, lower thresholds may be achieved which reduces the consumption of the device's power supply thereby promoting increased longevity of the device.

FIG. 7 depicts an exemplary graph 200 illustrating the amplitude of therapy stimulation energy during discharge of the energy stored in a plurality of output capacitors. The horizontal (X) axis of the graph 200 represents time in seconds and the vertical (Y) axis represents stimulation amplitude in volts. The stimulation amplitude is the energy discharged from the output capacitors during delivery of a therapy to a patient.

A first trace 202, shown as a solid line, represents the therapy stimulation waveform generated by a conventional delivery circuit 600 where three capacitors are coupled, typically hardwired, in series from the beginning of the delivery of the therapy until the stimulation pulse is delivered as desired for the given therapy. The trace 202 illustrates the therapy stimulation waveform as a truncated exponential waveform having a nearly instantaneous inclined leading-edge from zero volts to the maximum amplitude, 1400 volts in this case, with a gradual decay over a period of approximately 4 ms. This trace 202 is representative of the profile of a conventional therapy stimulation waveform and is based on the behavior of the output capacitors (i.e., I=C(dV/dt)), where "i" is the instantaneous current through the capacitor, "C" is the capacitance of the capacitors in Farads, and dV/dt is the instantaneous rate of voltage change in volts per second.

Trace 204, shown as a dotted line, is an exemplary therapy stimulation waveform that may be generated by the therapy delivery circuits described in accordance with aspects of the present disclosure. In particular, the waveform corresponds to the discharge of energy in the output capacitors 62 during the three phases described in conjunction with the circuit of FIG. 6. The trace 204 is illustrated as a stimulation therapy waveform having a stepped or ramped leading edge. Unlike the truncated exponential waveform of trace 202, the ramped leading edge of the waveform represented by trace 204 has been observed to more closely mimic a profile of the cardiac cell response time. In the case of cardiac cells, for example, the capacity for cells to respond to stimulation energy gradually increases over a period of time leading to capture. As such, an optimal therapy stimulation waveform is one that increases gradually over a period of time, with the stimulation energy increasing from zero to the maximum amplitude that achieves capture, 1200 volts in this case. This waveform 204 is more efficient than the conventional waveform 202 in that the stimulation energy over a given period of time is reduced.

The exemplary trace 204 is depicted having a first step 206a and a second step 206b to define three segments "A", "B", and "C". The first segment A coincides with the discharge of a first of the three output capacitors during the first phase of the therapy delivery. In the second segment B, a second of the three output capacitors is coupled in series to the first capacitor. Therefore, the second segment coincides with the discharge of the first and second capacitors coupled in series during the second phase of therapy delivery. In the third segment C, a third capacitor is coupled in series to the serially coupled first and second capacitors so that all three capacitors are coupled in series. This third segment coincides with the discharge of the output capacitors in the third phase.

In the illustrative embodiment, the time interval between the series coupling of the second capacitor to the first capacitor and the series coupling of the third capacitor to the serially connected first and second capacitors is depicted along the X axis. As is illustrated in the graph 200, the first and second intervals determine the magnitudes of each of the segments A, B, and C of the stepped leading edge of trace 204. The slope of trace 204 may also be manipulated based on the duration of the first and second intervals.

The amount of energy delivered to the patient by the conventional circuit can be calculated by determining the area under the curve of trace 202 whereas the amount of energy delivered to the patient in accordance with aspects of the present disclosure can be calculated by determining the area under the curve of trace 204. As is illustrated in the graph 200, the area under the curve of trace 202 is greater than the area under the curve of trace 204. This illustration shows that the stimulation energy required to achieve capture when therapy is delivered through the conventional circuit (202) is relatively larger in comparison to the stimulation energy required to achieve capture when delivered through the delivery circuit of the present disclosure (204).

The inventors have theorized that one of the underlying reasons for the decrease in the maximum amplitude arises from the ability to generate a stimulation waveform that mimics the cell response profile. Because the stimulation waveform is adapted to stimulate the cells during optimal times, an excess amount of energy does not have to be provided to compensate for the delayed cell response.

Therefore, the delivery circuit of the present disclosure exhibits a decrease in the stimulation energy that is delivered through the tissue of the patient. In addition to the significantly lower amplitude discussed above, the reduced stimulation energy facilitates a reduction in tissue trauma to the patient in comparison to the conventional delivery circuit. Moreover, relatively less energy is consumed for delivery of therapy by the delivery circuit of the present disclosure because of the reduced stimulation energy which also means that the capacitors can be charged up to the full power supply faster in relation to the conventional delivery circuit. The decreased consumption promotes an increase in the response time to cardiac conditions requiring stimulation therapy. The reduction in the energy requirement for delivery of stimulation therapy also promotes an increase in the device longevity.

Figure 8:
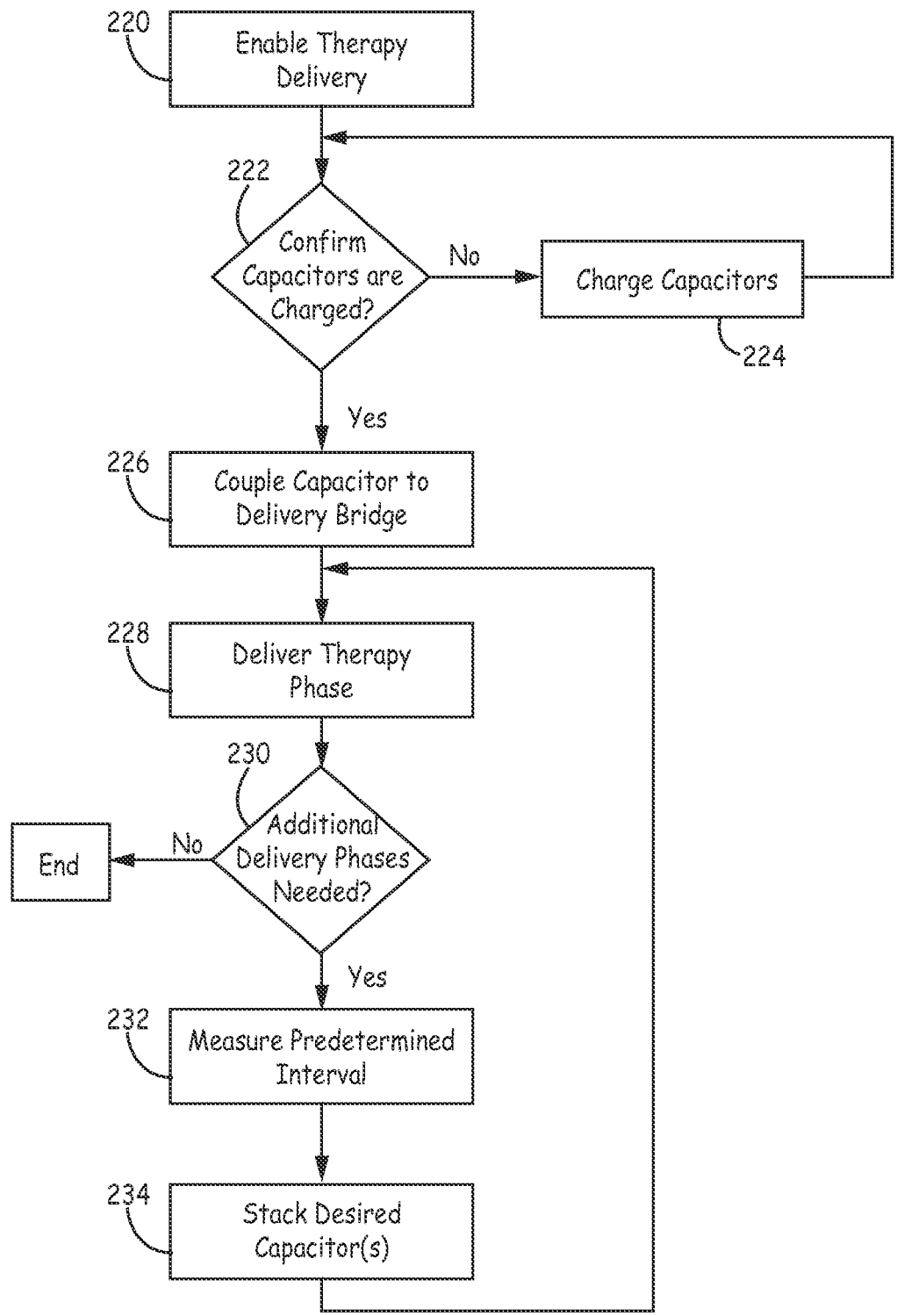
FIG. 8 is a flow chart depicting therapy delivery in accordance with an embodiment of this disclosure.

FIG. 8 is a flow chart depicting therapy delivery tasks in accordance with an embodiment of this disclosure. For illustrative purposes, the following description of the process in FIG. 8 may refer to elements mentioned above in connection with FIGS. 3 to 7. In practice, portions of the process may be performed by different elements of the described system; e.g., implanted sensors, an IMD, or an external monitoring device.

The flow chart in FIG. 8 describes the delivery of a therapy regimen, such as pacing, defibrillation, or cardioverting stimulation that may take the form of a stimulation pulse, a continuous waveform, or the like, from energy stored in the output capacitors. If therapy is not currently enabled, therapy can be initiated by a clinician, the patient, or the device (220). Finally, the device may automatically initiate therapy based on preprogrammed time of day or due to sensor signals, including electrograms, hemodynamic, activity sensor signals, and other physiologic sensor signals. In particular, a signal sensed by the device sensors may be evaluated to determine whether to initiate therapy deliver.

At task 222, the output capacitors that are configured to hold the charge for delivery of the therapy are monitored to determine whether sufficient energy is available for delivery of therapy. If it is determined that the capacitors are not charged up to the appropriate level, the charging circuit is operated to supply the power required to charge up the capacitor to the appropriate level (224).

Upon confirmation that the capacitors are charged up to the desired level, the delivery circuit initiates the discharge of the output capacitors in accordance with the programmed parameters. In an exemplary embodiment, a first output capacitor is coupled to the delivery bridge to initiate a first phase of therapy stimulation delivery through the selected electrode (226). The delivery control circuit may be programmed to determine the duration over which the first output capacitor is discharged. The delivery circuit discharges the given output capacitor through the delivery bridge for the programmed duration to deliver the given phase of the therapy stimulation (228).

Prior to, or during delivery of therapy in the first phase, the delivery control circuit determines whether additional phases are necessary for the given therapy regimen (230). For purposes of illustration, the therapy delivery may be preprogrammed to be provided in three phases in an exemplary embodiment.

The timing of the coupling of the subsequent capacitors to stack each individual subsequent capacitor to the previously discharging capacitor in a series configuration may be preprogrammed with the instructions being carried out by the delivery control circuit (232). In the exemplary embodiment, the delivery circuit couples a subsequent capacitor in series with the capacitor that has previously been coupled to the delivery bridge to initiate the next phase of the delivery of therapy (234).

The discharge of the series-coupled capacitors is performed for the subsequent phase of the therapy delivery. FIG. 8 depicts task 234 leading back to task 228; this loop represents the number of delivery phases that may be built in to the delivery of the therapy. Each successive coupling and discharge of the individual capacitors results in a stimulus pulse having a stepped leading edge waveform. The resulting waveform is a coarse ramp where the number of capacitors determines the number of steps and the slope of the leading edge is determined by the timing of the interval between stacking of the output capacitors (i.e. step delay). In response to determining that the requisite number of phases has been delivered, and that the therapy has been provided in accordance with preprogrammed parameters the therapy delivery may be terminated in any desired manner such as by decoupling the output capacitors from the delivery bridge.

The dynamic configurability of the stacking of the output capacitors 62 and the intervals between successive coupling of the individual capacitors 62 provides for manipulation of the waveform profile of the ramped leading edge. The slope of the ramped leading edge may also be controlled by the programmability of the intervals between the successive coupling of the individual output capacitors. For example, the slope of a first ramped leading edge is less steep in an implementation in which the coupling of the output capacitors 62 is performed following larger intervals compared to the slope of a second ramped leading edge for an implementation in which the coupling of the output capacitors 62 is performed following smaller intervals.

In comparison to the truncated exponential waveforms, the ramp waveforms generated in accordance with aspects of the present disclosure has exhibited reductions in the energy required for capture. The reductions have been in excess of 25%. The inventors have theorized that a leading factor for the reduction in threshold energies is the response time for the tissue cells to which the therapy is delivered. By delivering therapy in the form of a waveform that mimics the cell response time, an optimal amount of energy can be provided to the cells at the optimal response time.

Figure 9:
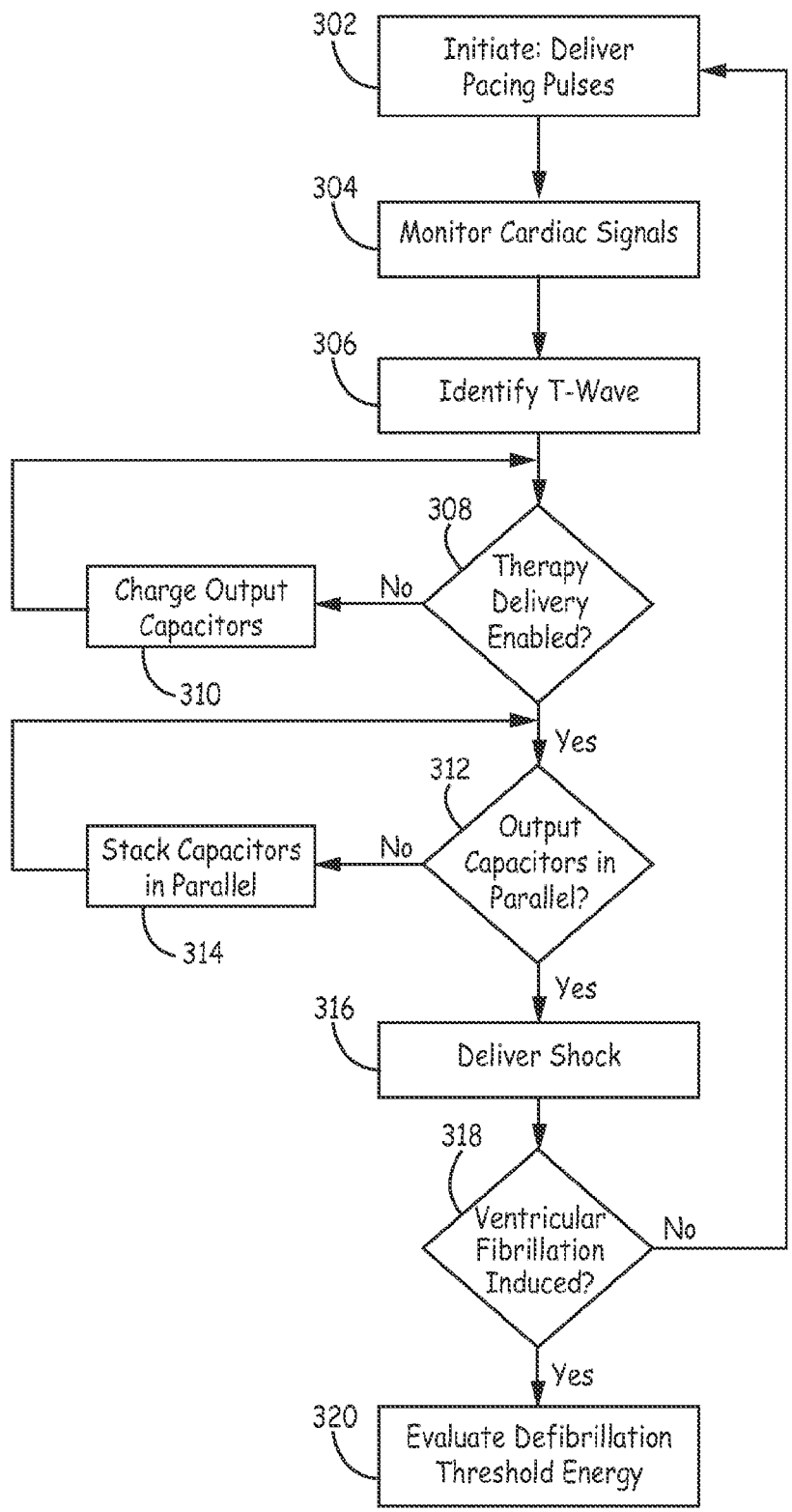
FIG. 9 is a flow chart of a method for determining a defibrillation threshold in accordance with an embodiment of this disclosure.

FIG. 9 is a flow chart of a method for determining a defibrillation threshold in accordance with an embodiment of this disclosure. The method may utilize devices described in accordance with embodiments of this disclosure to induce fibrillation and to subsequently determine a threshold amount of energy for terminating the fibrillation.

At task 302, pacing pulses may be delivered to the patient's heart at a desired pacing pulse energy and desired pacing rate. The pacing pulses may be delivered by device 14 or any other device capable of generating the pacing pulses.

During the pacing, the electrical conduction of the patient's heart may be monitored to obtain cardiac signals indicative of the heart's electrical conduction (304). The cardiac signals are evaluated to identify the occurrence of the T-wave and, in particular, the ascending part of the T-wave (306).

The method determines whether the therapy delivery source is enabled so as to initiate delivery of the energy stored by the output capacitors 62 for generating a stimulation pulse (308). Among other things, the therapy delivery is disabled if the output capacitors are not adequately charged. As such, the output capacitors may be charged to store the energy that is delivered to generate the stimulation pulse (310). A charge signal may be provided that indicates that the output capacitors have been charged up to a predetermined level.

The present disclosure facilitates the dynamic configuration of the capacitors 62 in any desired stacking arrangement. In embodiments in which the capacitors are stacked in a series configuration during charging, the output capacitors are stacked in a parallel configuration for delivery of the stimulation pulse to induce ventricular fibrillation. A determination may be made as to whether the stacking configuration of the plurality of capacitors is a parallel configuration (312). If not, the capacitors are subsequently stacked in parallel (314).

The method may be configured to provide a desired number of pacing pulses for synchronizing a stimulation pulse prior to delivery of the stimulation pulse. The stimulation pulse may be in the form of a low energy or subthreshold shock. In embodiments utilizing a pacing source other than device 14, the pacing source is disconnected, based on a specified number of delivered pulses, a predetermined time delay or other timing mechanism, prior to delivery of the stimulation pulse.

In response to identifying the occurrence of the T-wave, the stimulation pulse is delivered to the patient coinciding with the ascending part of the T-wave (316).

At task 318, the patient's electrical activity is evaluated to determine whether the delivered stimulation pulse successfully induced ventricular fibrillation. Onset of the ventricular fibrillation may be identified based on the patient's cardiac signals following the stimulation pulse delivery. If the initial stimulation pulse fails to induce ventricular fibrillation, tasks 302-318 may be repeated for as many iterations as necessary, with a different amount of energy in each iteration, until the ventricular fibrillation is induced.

Following successful induction of the ventricular fibrillation, the output capacitors may be recharged and reconfigured for determination of the threshold amount of energy that terminates the ventricular fibrillation (320). The charging and configuration of the output capacitors for delivery of the defibrillation energy may correspond to techniques described elsewhere in this disclosure.

The flow charts, techniques and technologies presented herein are intended to illustrate the functional operation of an exemplary device, and should not be construed as reflective of a specific form of software, firmware or hardware necessary to practice the invention. It is believed that the particular form of software, firmware, and hardware will be determined by the particular system architecture employed in the external pacing source, external shock source and interface and by the stimulation therapy (pacing and shock) delivery methodologies employed by external sources. For example, an embodiment of a system or a component may employ various integrated circuit components, e.g., memory elements, digital signal processing elements, logic elements, look-up tables, or the like, which may carry out a variety of functions under the control of one or more microprocessors or other control devices. To the extent that there is any ambiguity or inconsistency between the text and the circuit symbols depicted in the figures, the figures will be deemed to control.

Providing software, firmware and hardware to accomplish the present invention, given the disclosure herein, is within the abilities of one of skill in the art. For the sake of brevity, conventional techniques related to ventricular/atrial pressure sensing, IMD signal processing, telemetry, and other functional aspects of the systems (and the individual operating components of the systems) may not be described in detail herein. The methods described in conjunction with flow charts may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

The connecting lines shown in the various figures contained herein are intended to represent example functional relationships and/or physical couplings between the various elements. It should be noted that many alternative or additional functional relationships or physical connections may be present in an embodiment of the subject matter. Furthermore, it should be appreciated that the processes may include any number of additional or alternative tasks, the tasks shown in FIGS. 8 and 9 need not be performed in the illustrated order, and the process may be incorporated into a more comprehensive procedure or process having additional functionality not described herein.

The description refers to elements or nodes or features being "connected" or "coupled" together. As used herein, unless expressly stated otherwise, "connected" means that one element/node/feature is directly joined to (or directly communicates with) another element/node/feature, and not necessarily mechanically. Likewise, unless expressly stated otherwise, "coupled" means that one element/node/feature is directly or indirectly joined to (or directly or indirectly communicates with) another element/node/feature, and not necessarily mechanically. Thus, although the schematics shown in the figures depict exemplary arrangements of elements, additional intervening elements, devices, features, or components may be present in an embodiment of the depicted subject matter.

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

What is claimed is:

1. An implantable medical system having electronic circuitry and an electrode coupled to the electronic circuitry, the electronic circuitry comprising:
   a microprocessor programmed to detect a predetermined event in response to signals received from the electrode;
   a controller coupled to the microprocessor, wherein the controller is programmed to generate a control signal in response to detection of the predetermined event; and
   a delivery circuit coupled between the controller and the electrode, the delivery circuit including:
      a plurality of capacitors;
      a coupling circuit connected to the plurality of capacitors and operable to dynamically stack the plurality of capacitors in a first configuration during a first period that is coincident with the ascending part of the T-wave to induce ventricular fibrillation,
   recharge the plurality of capacitors in the first configuration, and
   subsequent to recharging the plurality of capacitors, reconfigure the stacking of the plurality of capacitors into a second configuration that is different from the first configuration during a second period and deliver stimulation therapy in response to an onset of the induced ventricular fibrillation in the second configuration.

2. The implantable medical system of claim 1, wherein the coupling circuit configures a second of the plurality of capacitors to be serially stacked onto the first capacitor for discharge of energy during a second of the intervals.

3. The implantable medical system of claim 2, wherein the coupling circuit controls a timing of the stacking of the second capacitor for discharge of energy from the first and second capacitor to generate a stimulation waveform having a stepped leading-edge.

4. The implantable medical system of claim 2, wherein the controller is operable to control the duration between the discharge of the first capacitor to the coupling of the second capacitor.

5. The implantable medical system of claim 1, wherein the coupling circuit comprises:
   a control module;
   a first switch coupled to a first of the plurality of capacitors and to the controller;
   a second switch coupled to a second of the plurality of capacitors and to the controller; and
   a third switch coupled between the first and second capacitors and to the controller, wherein the third switch is selectively actuated to stack the first and second capacitors serially.

6. The implantable medical system of claim 1, further comprising a delivery bridge coupled between the delivery circuit and the electrode.

7. The implantable medical system of claim 6, wherein the delivery circuit controls the timing and sequence of the coupling of the plurality of capacitors for discharge to the delivery bridge.

8. The implantable medical system of claim 7, wherein the timing and sequence of the coupling is controlled to generate a therapy stimulation waveform having a predetermined slope.

9. The implantable medical system of claim 6, wherein the delivery circuit controls the discharge of the plurality of capacitors through the delivery bridge.

10. The implantable medical system of claim 1, further comprising a diode coupled between the plurality of capacitors for biasing a direction of flow of charge from the plurality of capacitors.

11. The implantable medical system of claim 1, wherein the first period corresponds to a duration of charging the plurality of capacitors and the second period corresponds to a duration of therapy delivery in which energy stored in the plurality of capacitors is discharged.

12. The implantable medical system of claim 11, wherein the therapy delivery is initiated by coupling the plurality of capacitors to the electrode.

13. The implantable medical system of claim 1, wherein the coupling circuit includes:
   a control module;
   a plurality of stacking circuit modules coupled to the controller, each stacking circuit group including:
      a discharge FET and a switch coupled to a first terminal of one of the plurality of capacitors; and
      a gate trigger FET coupled between the controller and the switch.

14. The implantable medical system of claim 13, wherein the number of the plurality of stacking circuit modules corresponds to the number of the plurality of capacitors minus one.

15. The implantable medical system of claim 1, wherein the first configuration is a parallel configuration and the second configuration is a series configuration.

* * * * *